United States Patent [19]
Wolfram et al.

[11] Patent Number: 5,032,138
[45] Date of Patent: Jul. 16, 1991

[54] CHLORITES AS OXIDANTS IN HAIR COLORING

[75] Inventors: Leszek Wolfram, Stamford, Conn.; Thomas Schultz, Highland Mills, N.Y.; Alice Mayer, Bethel, Conn.; Keith Brown, New Canaan, Conn.

[73] Assignee: Clairol Incorporated, New York, N.Y.

[21] Appl. No.: 355,950

[22] Filed: May 23, 1989

[51] Int. Cl.[5] .............................................. A61K 7/13
[52] U.S. Cl. .............................................. 8/412; 8/406; 8/407; 8/408; 8/410; 8/421; 8/429
[58] Field of Search .............................................. 8/406-424

[56] References Cited

U.S. PATENT DOCUMENTS

| | | | |
|---|---|---|---|
| 3,214,472 | 10/1965 | Charle et al. | 260/571 |
| 3,236,734 | 2/1966 | Charle et al. | 260/571 |
| 3,241,722 | 3/1966 | Nissen | 222/146.3 |
| 3,869,454 | 3/1975 | Lang et al. | 8/405 |
| 3,985,499 | 10/1976 | Lang et al. | 8/416 |
| 4,103,772 | 8/1978 | Wiegner | 206/222 |
| 4,151,162 | 4/1979 | Lang et al. | 8/409 |
| 4,170,452 | 10/1979 | Grollin et al. | 8/406 |

OTHER PUBLICATIONS

Zviak, The Science of Hair Care, Chapters 7 and 8, pp. 235-286, (1986).

Venkataraman, The Chemistry of Synthetic Dyes, vol. V, Chapter VII: Corbett, "Hair Dyes", pp. 475-534 (1971).

*Primary Examiner*—A. Lionel Clingman
*Assistant Examiner*—J. E. Darland
*Attorney, Agent, or Firm*—Charles J. Zeller

[57] ABSTRACT

The invention provides compositions and methods for oxidative hair dyeing utilizing a chlorite salt as the oxidizing agent.

22 Claims, No Drawings

CHLORITES AS OXIDANTS IN HAIR COLORING

FIELD OF THE INVENTION

This invention concerns methods and compositions for dyeing human hair.

BACKGROUND OF THE INVENTION

Modern hair dyeing methodology has developed from its initiation in the 1950's to the point where, today it is the third largest product type in the hair care category following shampoos and conditioners.

The most commonly used method of dyeing hair, particularly human hair, is oxidative dyeing in which a mixture of aromatic compounds, generally of the benzenoid series, containing a plurality of nuclear amino and hydroxy functions, and which are themselves colorless, are converted by coupling reactions well known to those skilled in the art to a blend of colored compounds within the hair fibers by oxidative processes. The colorless aromatic compounds, in a suitable base formulation, normally are mixed with hydrogen peroxide or other strong oxidizing agent shortly before use. The colored compounds or dyes are, typically, formed by oxidative coupling between primary intermediates (usually diamino benzenes or amino phenols) and couplers which are phenols or related cyclic compounds. Various shades are developed by using a mixture containing more than one of both the intermediate and the coupler.

The intermediates and couplers because of their low molecular weights and water solubility diffuse easily into the hair where the coupling reaction takes place. The colored products developed by oxidation, however, remain trapped in the hair by virtue of their higher molecular weights, relative insolubility in water and absorptive affinity to the internal hair surface. This is the basis for permanent tints and toners which, ideally, last for the life of the hair and are relatively unaffected by shampooing and perspiration. Although permanence is the desideratum of the hair colorist, in practice it is difficult to achieve.

Another type of hair dyeing is direct dyeing in which the dye is deposited, and colors the keratinous fibers. Typical direct dyes include, for example, nitroaminophenols, nitrophenylenediamines, azo dyes, anthraquinones and nitroaminophenylethers.

One of the chief disadvantages of conventional oxidative dyeing is that the oxidant most often used is hydrogen peroxide. Although this chemical has the advantage of being harmless to the skin and inexpensive, it has the severe disadvantage of destructively oxidizing the hair keratin, causing oxidative and bleaching damage to the hair.

Moreover, hydrogen peroxide is normally used under alkaline conditions using ammonia or an amine as the alkaline reagent. These bases impart strong odors to the hair dyeing compositions to which many users strongly object.

Other oxidants have been suggested in attempts to avoid the problems of using hydrogen peroxide.

For example U.S. Pat. No. 2,944,869 teaches the use of orthophenols with alkali metal iodates, periodates and persulfates to form color in hair. U.S. Pat. No. 3,698,852 suggests that combinations of DOPA derivatives and arylamine derivatives in mixture with alkaline $H_2O_2$ dyes hair permanently. The patent also teaches that chlorate ($ClO_3^-$) salts can be employed with or without peroxide. It is required that the couplers be catechols.

U.S. Pat. No. 3,838,966 teaches that periodate and permanganate are useful for oxidizing lower valency metal ions to their oxides. The process may be carried out in the hair to color the hair permanently. No organic dyes are used, rather the hair dyeing is by the colored metal oxides.

U.S. Pat. Nos. 3,948,596 and 3,961,879 teach the oxidation of novel aminophenols with peroxide, persulfate or perborate to color hair.

U.S. Pat. No. 3,986,825 teaches that persulfates or percarbonates may be used in a permanent waving neutralizer that also contains oxidative dyes in the setting solution. This gives concurrent permanent-waving and coloring.

U.S. Pat. No. 4,104,021 claims various compositions using perborate, periodate or percarbonate in oxidation dye mixtures incorporating a polymer/conditioner.

None of these oxidative compositions have achieved the success of hydrogen peroxide containing oxidizing compositions.

The art has long sought dye compositions which will produce colors having lasting wear quality and will not cause oxidative and bleaching damage to the hair.

SUMMARY OF THE INVENTION

Oxidative hair dyeing compositions and methods for their use have now been discovered which avoid the disadvantages of damaging the hair. These novel compositions are characterized by the use of chlorite salts as the oxidizing agent in lieu of hydrogen peroxide.

There are many advantages to the compositions and methods of the invention. These include, for example:

1. The actual coloring of the hair is performed at a pH which is at, or close to, neutrality rather than under the strongly basic condition associated with the use of hydrogen peroxide-ammonia or amine combinations.
2. The odor is markedly reduced because of the absence of ammonia or an amine.
3. Chlorite salts do not bleach or cause other oxidative damage to human hair as does hydrogen peroxide.
4. The presence of the alkali metal chlorite in the compositions permits utilization of primary intermediates which could not be usefully employed with hydrogen peroxide, thus raising the possibility of new and heretofore unavailable tints and hues in the treated hair.
5. The wear quality of the colors produced in the dyed hair is appreciably enhanced as will be shown later.

Although this invention is generally applicable to chlorites, particularly metal chlorites such as alkali and alkaline earth metal chlorites, it will be principally described as it applies to the use of sodium chlorite. This reagent is by far the most preferred because it is very effective, soluble in water and aqueous alkanols, easily available in a purified state and relatively inexpensive. Additionally, it is substantially non-toxic. The $LD_{50}$ in rats is 140 mg/kg. Because it does not degrade the dyes formed by the coupling reaction, the color produced in its presence has outstanding wear qualities.

It is surprising to find that sodium chlorite is so very effective as an oxidant in hair dye compositions. The following Table 1 lists the electrochemical oxidation potentials of sodium chlorite together with oxidants such as those discussed above which have been employed in hair dye compositions.

TABLE 1

| Electrochemical Half-Wave Oxidation Potentials Of Common Oxidants | |
|---|---|
| OXIDANT | POTENTIAL ($E_{\frac{1}{2}}$) |
| Bromate | 1.52 |
| Hypochlorite | 1.64 |
| Chlorite | 0.59 |
| Perchlorate | 1.32 |
| Hydrogen Peroxide | 1.77 |
| Iodate | 1.11 |
| Periodate | 1.70 |
| Permanganate | 1.68 |
| Persulfate | 2.10 |

It will be noted that the oxidation potentials of all oxidants listed, except the chlorite are close to or exceed that of the most common oxidant, hydrogen peroxide. The potential of the chlorite, on the other hand is only one third that of hydrogen peroxide and yet hair dyeing compositions containing it not only are operable, but additionally have many advantages over comparable compositions containing hydrogen peroxide.

The compositions of this invention and their method of use are similar to previously known compositions and methods except for the use of a chlorite salt as the oxidant.

DETAILED DESCRIPTION OF THE INVENTION

The compositions of this invention as applied to the human hair, either living or in a wig or other artificial device with implanted human hair, will comprise a carrier vehicle usually water or water containing a lower alkanol such as ethanol or isopropanol to aid solubility, together with the selected primary intermediate and coupler, or a plurality of each, (hereinafter sometimes identified as the reactants) together with from about 0.1 to 20%, preferably 0.5 to 6% by weight of chlorite salt. All percent by weights defined in this disclosure and claims are percents by weight based on the total weight of the composition.

The amount of dye(s) or coupler(s) employed will be about the same as utilized in conventional oxidant compositions. The amounts which will be tinctorially effective will vary with the selected reactants as is well known in the art. Since the amounts will not vary appreciably from those employed with ordinary oxidant compositions containing hydrogen peroxide, the skilled artisan will have no difficulty in selecting the reactants and the amounts to be employed. Generally each reactant will be present in an amount of from about 0.1% to 3%.

The oxidant will be separately formulated to mix with the other components just prior to use as illustrated in the examples. Thus a product of the invention may comprise a package containing two separate units or aqueous compositions, one containing the oxidant, the other containing a primary intermediate and a coupler. The term "package" is used in the widest possible sense. It includes retail packages such as might be sold to an individual consumer with both compositions in the same box or other container. It includes also separate compositions in large amounts such as might be sold to a beauty salon whether or not the separate compositions are sold in the same container and are intended to be used together.

The compositions of this invention are particularly adapted for codispensing from a compartmentalized package such as the containers described in U.S. Pat. Nos. 3,241,722 and 4,103,772 the disclosures of which are incorporated herein by reference. In such codispensing packages, which have been employed previously with hydrogen peroxide dye systems, the reactants are normally sealed in one compartment of the container and the hydrogen peroxide in another, and the container is constructed with means for mixing the separate ingredients in the container and for the resulting composition to exit the container after such mixing.

There are two procedures for mixing which are normally employed. One utilizes an aerosol package and valve adapted so that the compositions in the compartments mix as they pass through the valve. In the other, the partition between the compartments is frangible and the container is formed with a mechanism so that the partition can be pierced or otherwise broken so that the compositions can mix prior to dispensing. Depending upon the design of the container, the resulting mixed composition can be dispensed under aerosol pressure, by simple pouring or by any other convenient method.

When such codispensing containers are employed with hydrogen peroxide systems, there is always danger of premature mixing by accidental leakage through the partition. As a result the dye forming reaction which is intended to take place in the open air takes place in a closed container thereby generating volumes of oxygen which may result in explosive pressures. There is no such danger when the oxidative salts of this invention are employed since the dye forming reaction does not generate oxygen.

Any of the conventional dyes and coupling agents used with ordinary oxidant compositions for hair coloring can be employed in the compositions of this invention to achieve a wide variety of tints and hues. Typically useful primary intermediates and couplers are mentioned, for example in U.S. Pat. Nos. 3,536,436; 4,092,102; 3,884,627; 3,981,677 and British Patent 2,205,329, incorporated by reference herein.

A wide variety of primary intermediates can be employed in this invention including, for example, paraphenylenediamines, corresponding to the formula:

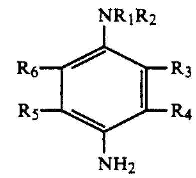

in which:

$R_1$ and $R_2$, which may be identical or different, can denote hydrogen, a $C_1$–$C_6$ lower alkyl group, a $C_1$–$C_6$ alkyl radical substituted with one or more hydroxy group(s) or with a methoxy, methylsulphonylamino or aminocarbonyl group, a furfuryl group, or a phenyl radical optionally substituted with an amino group; $R_3$ and $R_6$ can denote, independently of one another, hydrogen, a $C_1$–$C_6$ lower alkoxy group, a halogen atom such as a chlorine atom, a $C_1$–$C_6$ lower alkyl group, or a $C_1$–$C_6$ lower alkyl group substituted with one or more hydroxy group(s): and $R_4$ and $R_5$ denote, independently of one another, hydrogen, a $C_1$–$C_6$ lower alkoxy group, a $C_1$–$C_6$ lower alkyl group, or a halogen atom such as chlorine, as well as their salts with inorganic or organic acids, N,N'-diphenylalkylenediamines in which the phenyl groups are substituted at the para position with an OH or amino group optionally substituted with a $C_1$–$C_6$ alkyl group, it being possible for the amino groups joined by the alkylene group to be substituted with $C_1$–$C_6$ alkyl, $C_1$–$C_6$ hydroxyalkyl or $C_1$–$C_6$ aminoalkyl, para-aminophenols, ortho-aminophenols, orthophenylenediamines and heterocyclic oxidation bases.

Among the useful compounds of formula (I), there may be mentioned p-phenylenediamine, 2-methyl-para-phenylenediamine, 2-methoxy-para-phenylenediamine, 2-chloro-N-methyl-paraphenylenediamine, N-furfuryl-para-phenylenediamine, 3-methoxy-$N^1$-methyl-para-phenylenediamine, 2-chloro-para-phenylenediamine, N-methyl-para-phenylenediamine, 2,3-dimethyl-para-phenylenediamine, 5-chloro-$N^1$-methyl-p-phenylenediamine, 5-methyl-$N^1$,$N^1$,-dimethyl-p-phenylenediamine, 5-methyl-$N^1$-ethyl-$N^1$-(aminocarbonyl-methyl)-p-phenylenediamine, 5-methyl-$N^1$-ethyl-$N^1$-(methyl-sulphonylaminoethyl)-p-phenylenediamine, N-(2-methoxy-ethyl)-p-phenylenediamine, 2,6-dimethyl-p-phenylenediamine, N,N-bis(2-hydroxyethyl)-p-phenylenediamine. The N,$N^1$-diphenylalkylenediamines include, for example N,$N^1$-bis-(2-hydroxyethyl)-N,$N^1$-bis(p-aminophenyl)ethylenediamine. Their salts with acids such as the monohydrochlorides dihydrochlorides or sulphates are also suitable.

Among p-aminophenols which are more especially usable according to the invention, there may be mentioned p-aminophenol, 2-methyl-p-aminophenol, 2,3-dimethyl-p-aminophenol, 2,6-dimethyl-p-aminophenol, 3-methoxy-p-aminophenol 2-chloro-p-aminophenol, N-methyl-p-amino-phenol and 3-(methylthio)-p-aminophenol, of which p-aminophenol is preferred.

Among ortho bases, ortho-aminophenol, 5-chloro-orthoaminophenol and ortho-phenylenediamine are chosen more especially according to the invention.

Among heterocyclic bases, it is preferable, according to the invention, to use 2,3-diamino-6-methoxy-pyridine and 2-(2-hydroxyethyl)amino-5-aminopyridine and their salts, and still more especially 3,6-diaminopyridine, 2,6-dimethoxy-3-aminopyridine, 2-methylamino-3-amino-6-methoxypyridine, 2,5-diaminopyridine, 2-(N-hydroxyethyl)amino-5-amino pyridine, and 2-(N,N-bishydroxyethyl)amino-5-aminopyridine.

More especially preferred oxidation bases are p-phenylenediamine 2-methyl-p-phenylenediamine,N-(2-methoxyethyl)-p-phenylenediamine, N,N-bis(2-hydroxyethyl)-p-phenylene-diamine and p-aminophenol, mono- or polyhydroxylated derivatives of naphthalene and of aminonaphthalene, pyrazolones and benzomorpholines.

Among couplers or colour modifiers, there may be mentioned, in particular, the compounds corresponding to the formula:

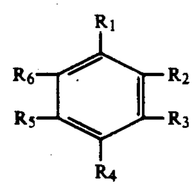

in which:

$R_1$ denotes hydroxy or an amino group which can be substituted with one or more $C_1$–$C_6$ hydroxyalkyl groups; $R_3$ and $R_5$, independently of one another, can denote hydrogen, a hydroxy group, an amino group optionally substituted with a $C_1$–$C_6$ lower hydroxyalkyl group or a $C_1$–$C_6$ lower alkyl group; and $R_2$, $R_4$ and $R_6$ can denote a hydrogen atom or a $C_1$–$C_6$ alkoxy group, a hydroxyalkoxy group or a $C_1$–$C_6$ lower alkyl group; it also being possible for $R_3$ and $R_4$ together to form a methylenedioxy group.

Among the suitable couplers, there may be mentioned 2-methoxy-5-aminophenol, 2-methoxy-5-[N-(2-hydroxyethyl)amino]phenyl, 1,3-diamino-2,6-dimethoxybenzene, 2-methoxy-1-(N-methylamino)-4-(2-hydroxyethoxy)-3-amino-benzene, 1,3-diamino-6-methoxybenzene, 1,3-diamino-4,6-dimethoxybenzene, 4,6-dimethoxy-1,3-bis[N-(2-hydroxyethyl)-amino]benzene, 2,6-dimethoxy-3-[N-(2-hydroxyethyl)amino]-1-aminobenzene, 2,4-dimethoxy-3-[N-(2hydroxyethyl-)amino]-1-aminobenzene, 2-methyl-5-[N-(2hydroxyethyl)amino]phenol, 1,3-bis[N-(2-hydroxyethyl)amino]-4methoxybenzene, 3-amino-4-methoxyphenol, 3,4-methylenedioxy-1-aminobenzene, 2,6-dimethyl 3-[N-(2-hydroxyethyl)amino]phenol, 2,6-dimethyl-3-aminophenol, 4-ethoxy-1-amino-3-[N,N-bis(2-hydroxyethyl-)amino]benzene, (2,4-diaminophenoxy)ethanol, (2-amino-N-methyl-4-aminophenoxy)ethanol, 1-methoxy-2-[N-(2hydroxyethyl)amino]-4-aminobenzene, 3,4-methylenedioxy-6-methoxyphenol, 3-amino-6-methylphenol, 3,4-methylenedioxy-6-methoxyaminobenzene, 3-aminophenol, 1,3-dihydroxybenzene-4-(hydroxyethoxy)-1,3-phenylenediamine, 4,6-(dihydroxyethoxy)-1,3-phenylenediamine, and 1,3-phenylenediamine.

Other suitable couplers are 6-aminobenzomorpholine, 1-amino-7-naphthol, 6-hydroxybenzomorpholine, 1-naphthol, 1,3-dihydroxynaphthalene and 1,2-dihydroxy-benzene. Among heterocyclic couplers there may be mentioned 2,6-dihydroxypyridine, 2,6-diaminopyridine, 2-amino-4hydroxypyridine, 2-hydroxy-4-amino-pyridine, 2-hydroxy-5-aminopyridine, 2-amino-6-hydroxypyridine and the like. Included also are further derivatives of 2,6-diamino alkyl pyridines where the amino nitrogen of one or both amino groups is mono- or disubstituted with a $C_1$ to $C_6$ alkyl group such as the methyl, propyl, isopropyl, butyl, iso- or sec-butyl, pentyl, sec-pentyl neopoentyl, t-butyl, hexyl, 3-methyl pentyl or 4-methylpentyl groups. The amino groups of either the amino-4-hydroxy- or 2-hydroxy-4-amino-pyridines may also have mono- or di-$C_1$–$C_6$ alkylation on the nitrogen atoms.

The 2,6-amino-, or 4-amino-2-hydroxy- or 2-amino-4-hydroxy pyridine nitrogens may also either singularly or doubly be derivatized with alkoxy substituents of carbon lengths of 1 to 6 with specific mention of 2-hydroxyethyl, 3-hydroxypropyl, 4-hydroxybutyl, 5-hydroxypentyl, 6-hydroxyhexyl, 2-hydroxypropyl, 2-hydroxybutyl, 2-hydroxypentyl, 2-hydroxyhexyl, 3-hydroxybutyl, 3-hydroxypentyl, 2-hydroxyhexyl, 4-hydroxypentyl and 5-hydroxypentyl groups.

Among trihydroxylated derivatives of benzene, there may be mentioned 1,2,4-trihydroxybenzene, 1,2,4-trihydroxy-5-alkylbenzenes in which the alkyl group is a $C_1$–$C_6$ lower alkyl group and 1,2,3-trihydroxybenzene, and their salts.

Among diaminohydroxybenzenes, there may be mentioned 2,4-diaminophenol and 2,5-diamino-4-methoxy-1-hydroxybenzene, and their salts.

Among aminodihydroxybenzenes, there may be mentioned 2-amino-1,4-dihydroxybenzene, 1,4-dihydroxy-2-diethylaminobenzene and 4-aminoresorcinol, and their salts.

Among substituted 1,2-dihydroxybenzenes, 4-methyl-1,2-dihydroxybenzene and 3-methoxy-1,2-dihydroxybenzene are especially preferred.

The aminohydroxybenzenes are chosen, in partricular, from 2-amino-4-methoxyphenol, 2-aminophenol, 4,6-dimethoxy-3-amino-1-hydroxybenzene and 2,6-dimethyl-4-[N-(p-hydroxphenyl)amino]-1-hydroxybenzene, and their salts.

By way of a triaminobenzene, there may be mentioned 1,5-diamino-2-methyl-4-[N-(p-hydroxyphenyl-)amino]-benzene and its salts.

Table 2, below lists some of the preferred primary intermediates and couplers for use in this invention.

TABLE 2

| A List of Primary Intermediates and Couplers | |
|---|---|
| Primary Intermediates: | p-phenylenediamine |
| | p-aminophenol |
| | o-aminophenol |
| | N,N-bis(2-hydroxyethyl)p-phenylenediamine |
| | 2,5-diaminopyridine |
| | p-toluene diamine |
| Couplers: | resorcinol |
| | m-aminophenol |
| | α-naphthol |
| | 5-amino-o-cresol |
| | 2-methylresorcinol |
| | 5-amino-2-(N,N-dimethylaminomethyl)phenol |
| | 4,6-di(hydroxyethoxy)-meta-phenylenediamine meta-phenylenediamine |

The utility of chlorites in oxidative color formation from p-phenylene diamine and phenols can be seen readily by comparing the absorption maxima of dyes generated with chlorite or hydrogen peroxide. Table 3 lists the primary intermediate, coupler, oxidant and colors.

TABLE 3

Colors obtained from oxidative coupling of various primary intermediates and couplers by chlorite and alkaline hydrogen peroxide.

| Ex | Primary Intermediate | Coupler | Oxidant | Color Absorptionmaximum |
|---|---|---|---|---|
| 1 | p-phenylene-diamine | α-naphthol | $H_2O_2$ | violet (523 nm) |
| 2 | p-phenylene-diamine | α-naphthol | $NaClO_2$ | red-violet (500 nm) |
| 3 | p-phenylene-diamine | 4-(2-hydroxyethoxy)-1,3-phenylenediamine | $H_2O_2$ | blue-violet (528 nm) |
| 4. | p-phenylene-diamine | 4-(2-hydroxyethoxy)-1,3-phenylenediamine | $NaClO_2$ | blue-violet (525 nm) |
| 5. | p-phenylene-diamine | 4,6-bis(2-hydroxyethoxy)-1,3-phenylenediamine | $H_2O_2$ | blue-violet (533 nm) |
| 6. | p-phenylene-diamine | 4,6-bis(2-hydroxyethoxy)-1,3-phenylenediamine | $NaClO_2$ | blue-violet (50 nm) |
| 7. | N,N-bis-hydroxyethyl p-phenylenediamine | α-naphthol | $H_2O_2$ | blue (607 nm) |
| 8. | N,N-bis(2-hydroxyethyl) p-phenylenediamine | α-naphthol | $NaClO_2$ | violet-blue (595 nm) |
| 9. | N,N-bis(2-hydroxyethyl) p-phenylenediamine | 4-(2-hydroxyethoxy)-1,3-phenylenediamine | $H_2O_2$ | blue (628 nm) |
| 10. | N,N-bis(2-hydroxyethyl) p-phenylenediamine | 4-(2-hydroxyethoxy)-1,3-phenylenediamine | $NaClO_2$ | blue (637 nm) |
| 11. | N,N-bis(2-hydroxyethyl) p-phenylenediamine | 4,6bis(2-hydroxyethoxy)-1,3-phenylenediamine | $H_2O_2$ | blue (637 nm) |
| 12. | N,N-bis(2-hydroxyethyl) p-phenylenediamine | 4,6bis(2-hydroxyethoxy)-1,3-phenylenediamine | $NaClO_2$ | blue (632 nm) |

The reactants shown in Table 3 can be combined in compositions of the invention and used in accordance with the methods of the invention to produce the desired colors.

Well known conventional additives usually employed in oxidative hair coloring compositions such as thickeners, surface active agents, antioxidants, fragrances and chelating agents may be included in the compositions of the inventions. Such compositions are preferably liquid solutions but they may be in the form of emulsions, suspensions, lotions, or gels.

Surface active agents employed in the dyeing compositions of this invention can be anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethyl-benzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-diethyl tridecanol-6-sulfate and the like. The quantity of surface active agent can very over a wide range, such as from about 0.05% to 15% and preferably from about 0.10 to 5% by weight of the composition.

A thickening agent may also be incorporated in the dyeing composition of this invention which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.5 to 5% by weight of the composition. The viscosity of the composition may vary from about 1 cp to about 100,000 cps. For a typical lotion formulation, composition viscosity is between about 100 cps to about 10,000 cps.

It may also be useful to incorporate an antioxidant in the present dye compositions. A variety of antioxidants are known in the prior art which would be useful for this purpose. Among these mention may be made of the inorganic sulfites, e.g., sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc. The quantity of antioxidant when in use can vary quite a bit. However, this will, in general, be up to about 1%, typically 0.001 to 1% by weight.

The dyeing compositions of this invention are preferably aqueous compositions. The term aqueous composition is used herein in its usual generic sense as embracing any water-containing composition useful for the present purposes. This includes true solutions of the chlorite, primary intermediates and couplers in an aqueous medium, either alone or in conjunction with other materials, which are also dissolved or dispersed in the aqueous medium. The term aqueous composition also encompasses any mixture of the chlorite and the dye forming reactants with the aqueous medium either alone or together with other ingredients. The various components may be colloidally dispersed in the medium or may merely be intimately mixed therein. Moreover, the aqueous medium may comprise water or water and an additional or auxiliary solvent. Typical auxiliary solvents which may be used to enhance the solubility of the components include ethanol, carbitol, isopropanol, propylene glycol, ethylene glycol, diethylene glycol, diethylene glycol monoethyl ether, glycerine, etc.

The aqueous dyeing compositions of this invention can be prepared by conventional methods used in the hair dyeing art. Thus, they can be prepared by dissolving or suspending the components in the selected media with adequate mixing. Preparation may take place at ambient temperatures, i.e., 20° to 35° C., but solubility and rate of preparation can be enhanced utilizing elevated temperatures, for example 40° to 100° C.

In Table 4 are listed a number of typical compositions of the invention each comprising two separate solutions. The compositions listed in the Table are specific examples of compositions of the invention.

TABLE 4

Examples of hair dyeing with oxidation dye precursors using sodium chlorite as the developer. Blended grey hair is dyed by the colors listed in the table by combining equal parts of solution A with solution B, vigorously mixing the composition and applying the mixture to hair for 20 minutes. The hair is then rinsed. percent component designations are weight %.

| Example | | Solution A | Solution B | Hunter Chromicity Values | | |
|---|---|---|---|---|---|---|
| | | | | L | a | b |
| 1. | 0.2% | p-pheneylenediamine | 4 gm Sodium Chlorite | | | |
| | 0.4% | 5-amino-o-cresol | | | | |
| | 8.0% | ethanol | | 28.2 | 4.4 | 5.7 |
| | 91.4% | $H_2O$ | 96 gm $H_2O$ | color: light reddish brown | | |
| | 100.00 | | 100.00 | | | |
| 2. | 0.18% | p-phenylenediamine | | | | |
| | 0.12% | N,N-bis(2-hydroxyethyl)-p-phenylendiamine | as per example 1 | 18.7 | 1.6 | −0.9 |
| | 0.29% | resorcinol | | | | |
| | 0.05% | α-naphthol | | color: voilet grey | | |
| | 8.5% | isopropanol | | | | |
| | 90.86% | $H_2O$ | | | | |
| | 100.00% | | | | | |
| 3. | 0.2% | p-phenylenediamine | | | | |
| | 0.15% | N.N-bis(2-hydroxyethyl)-p-phenylenediamine | as per example 1 | 23.0 | 0.8 | 3.3 |
| | 0.39% | resorcinol | | | | |
| | 0.07% | α-naphthol | | | | |
| | 8.0% | isopropanol | | color: ash brown | | |
| | 3.0% | hydroxyethycellulose | | | | |
| | 88.19% | $H_2O$ | | | | |
| | 100.00% | | | | | |
| 4. | 0.5% | p-phenylenediamine | as per example 1 | | | |
| | 0.09% | N,N-bis(2-hydroxyethyl)-p-phenylenediamine | | | | |
| | 0.47% | resorcinol | | | | |
| | 0.07% | α-naphthol | | | | |
| | 0.49% | p-aminophenol | | | | |
| | 0.46% | 5-amino-o-cresol | | | | |
| | 8.0% | isopropanol | | 14.8 | 3.2 | 2.9 |
| | 0.1% | sodium sulfite | | | | |
| | 0.2% | erythorbic acid | | color: dark brown | | |
| | 0.02% | EDTA | | | | |
| | 3.0% | hydroxyethylcellulose | | | | |
| | 86.6% | $H_2O$ | | | | |
| | 100.0% | | | | | |
| 5. | 3.0% | p-phenylenediamine | | | | |
| | 0.66% | N,N-bis(2-hydroxyethyl) | as per example 1 | | | |

TABLE 4-continued

Examples of hair dyeing with oxidation dye precursors using sodium chlorite as the developer. Blended grey hair is dyed by the colors listed in the table by combining equal parts of solution A with solution B, vigorously mixing the composition and applying the mixture to hair for 20 minutes. The hair is then rinsed. percent component designations are weight %.

| Example | Solution A | Solution B | Hunter Chromicity Values L | a | b |
|---|---|---|---|---|---|
| | p-phenylenediamine | | | | |
| 1.7% | resorcinol | | | | |
| 1.67% | 5-amino-2-(N,N-dimethyl-aminomethyl)phenol | | | | |
| 0.08% | m-aminophenol | | | | |
| 0.1% | sodium sulfite | | | | |
| 0.02% | EDTA | | | | |
| 0.2% | erythorbic acid | | | | |
| 3.0% | diethyleneglycol | | 11.7 | 0.1 | 1.1 |
| 9.0% | isopropanol | | | black | |
| 3.0% | hydroxyethylcellulose | | | | |
| 77.6% | $H_2O$ | | | | |
| 100.0% | | | | | |

The Hunter chromicity values are standard values determined by means well known to those skilled in the art.

In the Hunter Tristimulus System, L is a measure of lightness and darkness, that is, the depth of the color of the hair tress. The lower the value of L, the darker the color.

The value of b is a measure of the blueness or yellowness of the hair color. As the b value increases, the hair tress is more yellow.

Table 5 summarizes the colors of blended grey hair using a variety of primary intermediates and couplers and sodium chlorite as the oxidant in accordance with the invention.

TABLE 5

A summary of the compositions of primary intermediates and couplers used in a dye base composed of hydroxyethylcellulose (3%, wt/wt), isopropanol (8%), erythorbic acid (0.2%), EDTA (0.02%) and water to qs of 100%. Dye percentages below are weight %. Color of dyed hair is also given. Blended grey with Hunter chromicity values of L = 35.2, a = −0.8, b = 6.9. Hair was dyed for 20 minutes (liquor:hair = 2) followed by rinsing and air drying.

| | INTERMEDIATES | | | | COUPLERS | | | | | | HUNTER CHROMICITY VALUES | | | |
|---|---|---|---|---|---|---|---|---|---|---|---|---|---|---|
| EXAMPLE | 1 | 2 | 3 | 4 | 5 | 6 | 7 | 8 | 9 | 10 | L | a | b | COLOR |
| 1. | 3.0 | | 0.66 | | 1.7 | 0.08 | | | | 1.67 | 11.7 | 0.1 | 1.1 | Black |
| 2. | 2.0 | | 0.44 | | 1.13 | 0.05 | | | | 1.11 | 12.4 | 0.6 | 1.1 | Dark Gray |
| 3. | 2.4 | | 3.0 | | | | | | | 3.0 | 15.5 | 0.9 | 0.4 | Violet Gray |
| 4. | 1.33 | | 0.29 | | 0.75 | 0.03 | | | | 0.37 | 13.6 | 1.0 | 1.5 | Dark Brown |
| 5. | 1.31 | | 1.47 | | 1.2 | 1.08 | | 0.2 | | | 14.0 | 0.6 | 2.1 | Dark Warm Brown |
| 6. | 3.43 | | 1.96 | | | 1.76 | 1.2 | | | | 12.9 | 0.3 | 1.7 | Dark Ash Brwn |
| 7. | 1.33 | | 0.29 | | 0.75 | 0.03 | 0.37 | | | | 14.5 | 1.0 | 2.3 | Med. Dark Bown |
| 8. | | | 0.36 | 0.69 | 0.61 | | 0.15 | | | | 16.5 | 0.4 | 1.8 | Gray Brown |
| 9. | | | 0.36 | 1.38 | 0.61 | | 0.15 | | | | 17.2 | 1.0 | 4.1 | Golden Brown |
| 10. | 0.14 | | 0.06 | | 0.2 | | 0.08 | | | | 20.0 | 1.2 | 2.1 | H. gray bro |
| 11. | 0.12 | 0.37 | 0.01 | | 0.23 | | 0.01 | 0.42 | | | 20.1 | 3.7 | 4.7 | Light Auburn |
| 12. | 0.50 | 0.49 | 0.09 | | 0.47 | | 0.07 | 0.46 | | | 14.5 | 2.5 | 2.3 | Light Auburn |
| 13. | 0.18 | | 0.12 | | 0.29 | | 0.05 | | | | 20.9 | 1.1 | 3.3 | Light Brown |
| 14. | 0.20 | | 0.64 | | 0.88 | | 0.22 | | | | 17.1 | 0.4 | 0.1 | Gray-brown |
| 15. | 0.20 | | 0.15 | | 0.39 | | 0.07 | | | | 19.7 | 0.9 | 2.9 | Lt. Ash brown |
| 16. | 0.37 | 0.16 | 0.03 | | 0.29 | | 0.06 | | 0.40 | | 16.6 | 1.3 | 2.6 | Med. Reddish Br |
| 17. | 0.51 | | 0.24 | | 0.44 | | 0.14 | | | | 15.3 | 0.6 | 2.3 | Med. Brown |

1. p-phenylenediamine
2. p-aminophenol
3. N,N-bis(2-hydroxyethyl)-p-phenylediamine
4. 2,5-diaminopyridine
5. resorcinol
6. m-aminophenol
7. α-naphthol
8. 5-amino-o-cresol
9. 2-methyl resorcinol
10. 5-amino-2-(N,N-dimethylaminoethyl)phenol A decrease in the value of L indicates a darkening of the hair tress. In the case of bleached and blended gray hair, a lowering of L shows deposition of hair dye on the tress.

The a value is a measure of the greenness or redness of the hair's color. As the a value increases, the hair has a more prominent red tonality. A lowering in the a value results in greener shades.

Table 6, below shows the wear quality of the color produced with the compositions of this invention. It shows how the stability of the color of hair treated with the compositions of this invention under a variety of stress conditions as described in the table.

TABLE 6

A listing of the Tristimulus Values L, a and b before and after subjecting hair tresses (dyed with the composiition of Example 4 in Table 3) to various environmental conditions

| | Before | | | After | | |
|---|---|---|---|---|---|---|
| | L | a | b | L | a | b |
| Heat (50° C.-dry heat[a] 17 hours) | 14.0 | 2.9 | 2.2 | 14.0 | 2.8 | 2.5 |
| Moisture (50° C. overnight[b] saturated) | 14.6 | 3.1 | 2.6 | 13.6 | 3.2 | 3.6 |
| Window Light (7 days)[c] | 14.1 | 3.1 | 2.2 | 13.4 | 0.0 | 2.5 |
| Light (20 hrs. fadometer)[d] | 14.8 | 3.2 | 2.9 | 16.3 | 2.4 | 4.4 |

[a]Electrically heated oven with temperature control of ±0.5° C.
[b]Hair tresses were suspended in a sealed glass vessel containing a pool of water and the entire container warmed to 50° C. in an electrically heated oven with a temperature maintenance of ±0.50° C.
[c]Northern Light
[d]Tresses mounted on black paper and illuminated with an Atlas Fad-o-meter light source.

A particular benefit of the composition of this invention is that the chlorite does not damage the hair.

The amount of oxidative damage done to hair with use of chlorite is dramatically less than when hydrogen peroxide is used. Hydrogen peroxide is typically employed in oxidative hair coloring at alkaline pH and, the resulting mixture quite often damages hair. This is evidenced by a raspy and coarse feel. There are several methods to quantify these tactile properties one of which is to measure the amount of cysteic acid formed in the fiber after contact with the oxidant. Table 7 shows the results of several determinations of the amount of cysteic acid present after virgin hair was contacted with different oxidants. There is a dramatic increase in cysteic acid after treatment with both hydrogen peroxide and ammonium persulfate but none forms after the hair is soaked with 4% sodium chlorite. The same behaviour was observed when the hair was colored with a standard oxidation dye mixture using chlorite as the developer (Table 8).

TABLE 7

Effects of contacting hair with various oxidants. The second column lists the oxidants contacting the hair, the third the amount of cysteic acid present upon amino acid analysis of the hair.

| Ex. | Oxidant | um/g cysteic acid |
|---|---|---|
| 1. | none | 149 |
| 2. | 3% $H_2O_2$ pH 9.5 | 245 |
| 3. | 4% $NaClO_2$ pH 11 | 148 |
| 4. | 4% $NaClO_2$ pH 6 | 143 |
| 5. | 5% $NH_4S_2O_8$ | 165 |

The tests were done on natural unpigmented hair.
Contact time was 20 minutes at a 10:1 liquor to hair ratio.

TABLE 8

Amount of cysteic acid formed when hair is dyed with a commercial oxidation dye using either peroxide or chlorite as the developer.

| Ex. | Oxidant | um/g cysteic acid |
|---|---|---|
| 1. | none | 139 |
| 2. | $H_2O_2$ | 256 |
| 3. | $NaClO_2$ | 147 |

Another advantage of the chlorite is that it will form strong colors from primary intermediates which usually form no color or only weak colors with peroxide. This permits a much broader range with the compositions of this invention than is typically available. For example, 2,5-diaminopyridine, does not react with hydrogen peroxide in the presence of standard couplers to give intensely dyed hair. Table 9 shows the color of blended grey hair dyed with analogs of p-phenylenediamine using either hydrogen peroxide or sodium chlorite as the oxidant. Only the parent diamine dyes hair more intensely with hydrogen peroxide as the oxidant. The other compounds are only marginally effective as primary intermediates when $H_2O_2$ is used, but do form strong color with chlorite. Each dyeing trial was performed using equal mole percent primary intermediate to coupler ratios at a 0.7 wt percent composition in 8% isopropanol-92% water.

TABLE 9

Blended grey hair dyed with various p-phenylenediamine derivatives and resorcinal using either 6% hydrogen peroxide at pH 9 (adjusted with $NH_4OH$) or 4% sodium chlorite as the oxidant. The dying time, in all cases, was 20 minutes.

| | | | Hunter Colorimetric values | | |
|---|---|---|---|---|---|
| Ex | Intermediate | oxidant | L | a | b |
| 1. | 2,5-diaminopyridine | $H_2O_2$ | 29.4 | 1.8 | 6.1 |
| 2. | 2,5-diaminopyridine | $NaClO_2$ | 20.8 | 4.7 | 6.2 |
| 3. | o-chloro-p-phenylene-diamine | $H_2O_2$ | 28.7 | 0.3 | 6.0 |
| 4. | o-chloro-p-phenylene-diamine | $NaClO_2$ | 14.5 | 1.3 | 3.3 |
| 5. | 2-(N-hydroxyethyl)-amino-5-aminopyridine | $H_2O_2$ | 30.3 | 0.8 | 5.3 |
| 6. | 2-(N-hydroxyethyl)-amino-5-aminopyridine | $NaClO_2$ | 25.1 | 3.3 | 4.3 |
| 7. | 2-(N,N-bishydroxyethyl) amino-5-aminopyridine | $H_2O_2$ | 28.9 | 1.0 | 5.3 |
| 8. | 2-(N,N-bishydroxyethyl) amino-5-aminopyridine | $NaClO_2$ | 26.2 | 0.3 | 2.6 |
| 9. | 2-[(2-hydroxyethyl)-amino]-5-aminobenzonitrile | $H_2O_2$ | 29.0 | 1.5 | 6.1 |
| 10. | 2-[(2-hydroxyethyl)-amino]-5-aminobenzonitrile | $NaClO_2$ | 21.3 | 3.8 | 4.1 |
| 11. | 2-trifluoromethyl-p-amino-phenol | $H_2O_2$ | 33.5 | 0.3 | 7.9 |
| 12. | 2-trifluoromethyl-p-amino-phenol | $NaClO_2$ | 29.1 | 0.8 | 9.6 |

The methods of this invention are also applicable to heterocyclic couplers used in association with a variety of primary intermediates as shown in the following Table 10.

TABLE 10

Examples of blended grey hair dyed with different p-phenylenediamines and pyridine couplers using sodium chlorite as the oxidant.

| | Primary | | Hunter Colorimetric values | | |
|---|---|---|---|---|---|
| Ex | Intermediate | coupler | L | a | b |
| 1. | 1% p-phenylenediamine | 2% 2,6-dihydroxypyridine | 17.0 | 2.0 (reddish brown) | 1.0 |
| 2. | 1% p-phenylenediamine | 1% 2,6-diaminopyridine | 15.4 | −0.9 | −4.0 |

TABLE 10-continued

Examples of blended grey hair dyed with different p-phenylenediamines and pyridine couplers using sodium chlorite as the oxidant.

| Ex | Primary Intermediate | coupler | Hunter Colorimetric values L | a | b |
|---|---|---|---|---|---|
| 3. | 1% 2,5-diaminopyridine | 3.6% 2,6-dihydroxypyridine | 22.7 | (dark blue) −2.4 | 1.3 |
| 4. | none | 1% 2,6-dihydroxypyridine | 29.2 | (blue green) −1.8 | 3.2 |
| 5. | untreated blended grey (control) | | 35.6 | −0.7 | 7.3 |

All hair dyes in a total solution composition of 8% iso-propanol ad water q.s. to 100% for 20 minutes followed by rinsing.

Another advantage of the methods of the invention is that hair dyed with a mixture of primary imtermediates and couplers using a chlorite salt as the developer wears better than conventionally dyed hair. Table 11 shows the overall change in colorimetric value for bleached (damaged) and brown (virgin) hair dyed with a standard oxidative dye composition (using $H_2O_2$), or a standard semi-permanent composition and a standard oxidative dye mixture using sodium chlorite as the developer. The shade was similar in all cases. The dyed hair was exposed to artificial sunlight for 20 hours or washed through six repetitions of hand shampooing/rinse cycles or exposed for 22 hours to synthetic perspiration (1% NaCl, 0.1% lactic acid 0.025% histidine monohydrochloride, 0.1% di-sodium hydrogen phosphate at pH 3.5 with 1N HCL)

The total change in color is represented as Δ where Δ is defined by $\Delta=\sqrt{(a_i-a_f)^2+(b_i-b_f)^2+(L_1-L_f)^2}$ where i=initial reading and f=final reading.

TABLE 11

Effects of simulated environmental conditions on bleached and brown hair dyed with a standard oxidative dye composition using either hydrogen peroxide or sodium chlorite as the oxidant or using a standard or semi permanent dye. Change in color expressed as Δ;

$$\Delta = \sqrt{(a_i - a_f)^2 + (b_i - b_f)^2 + (L_1 - L_f)^2}$$

| | Hair Dye | Hair Type* | Light Exposure | 6× hand Shampoos | Synthetic Perspiration |
|---|---|---|---|---|---|
| 1. | oxidation-$H_2O_2$ as oxidant | BL | 2.4 | 2.1 | 3.3 |
| | | BR | 1.5 | 2.0 | 2.6 |
| 2. | oxidation-$NaClO_2$ as oxidant | BL | 0.4 | 0.5 | 2.4 |
| | | BR | 0.6 | 1.6 | 1.5 |
| 3. | semipermanent | BL | 3.6 | 20.6 | 16.9 |
| | | BR | 0.9 | 8.6 | 2.1 |

*BL = Commercially bleached
BR = Brown virgin hair

The methods and compositions of this invention are especially adapted to coloring the hair a shade equal to or darker than the natural color since the chlorite salts have no bleaching action. If a shade lighter than the natural color is desired the hair may be initially bleached and then dyed in accordance with the methods described herein.

What is claimed is:

1. An oxidative hair dye composition comprising an aqueous solution containing from about 0.1% to 20% by weight of an alkali or alkaline earth metal chlorite salt together with an amount of oxidative primary intermediate and coupler which will react to form a tinctorially effective amount of a hair dye.

2. An oxidative hair dye composition of claim 1 wherein the chlorite salt is sodium chlorite.

3. An oxidative hair dye composition of claim 2 wherein the amount of sodium chlorite is 0.5% to 6% by weight.

4. An oxidative hair dye composition of claim 1 further comprising at least one of the following: surface active agents in an amount up to about 15% by weight, thickening agents in an amount up to about 20% by weight, and antioxidant up to about 1% by weight.

5. An oxidative hair dye composition of claim 2 further comprising at least one of the following: surface active agents in an amount up to about 15% by weight, thickening agents in an amount up to about 20% by weight and antioxidant up to about 1% by weight.

6. An oxidative hair dye composition of claim 3 further comprising at least one of the following: surface active agents in an amount up to about 15% by weight, thickening agents in an amount up to about 20% by weight, and antioxidant up to about 1% by weight.

7. A package containing two separate compositions the first comprising an aqueous solution containing an alkali or alkaline earth metal chlorite salt the other containing in an aqueous composition an amount of an oxidative primary intermediate and a coupler which will react to form a tinctorially effective amount of hair dye composition, the amount of chlorite salt in the first composition being sufficient so that when the two compositions are mixed the amount of chlorite saltin the resulting composition is 0.1% to 20% by weight.

8. A package of claim 7 wherein the chlorite salt is sodium chlorite.

9. A package of claim 8 wherein the amount of sodium chlorite in the final composition is 2% to 6% by weight.

10. A package of claim 7 wherein the first two compositions additionally contain at least one of a surface active agent, a thickening agent and an antioxidant in an amount selected so that the resulting oxidative composition comprises at least one of the following: surface active agents in an amount up to about 15% by weight, thickening agents in an amount up to about 20% by weight, and antioxidant up to about 1% by weight.

11. A package of claim 8 wherein the first two compositions additionally contain at least one of a surface active agent, a thickening agent and an antioxidant in an amount selected so that the resulting oxidative composition comprises at least one of the following: surface active agents in an amount up to about 15% by weight, thickening agents in an amount up to about 20% by weight and antioxidant up to about 1% by weight.

12. A package of claim 9 wherein the first two compositions additionally contain at least one of a surface active agent, a thickening agent and an antioxidant in an amount selected so that the resulting oxidative composition comprises at least one of the following: surface active agents in an amount up to about 15% by weight, thickening agents in an amount up to about 20% by weight, and antioxidant up to about 1% by weight.

13. A package of claim 7, 8, 9, 10, 11 or 12 wherein the first and second compositions are in separate compartments of the same container, the container being constructed with means for mixing said compositions within the container to form the oxidative hair dye composition.

14. A method of dyeing hair comprising the step of applying to the hair an oxidative composition of claim 1.

15. A method of dyeing hair comprising the step of applying to the hair an oxidative composition of claim 2.

16. A method of dyeing hair comprising the step of applying to the hair an oxidative composition of claim 3.

17. A method of dyeing hair comprising the step of applying to the hair an oxidative composition of claim 4.

18. A method of dyeing hair comprising the step of applying to the hair an oxidative composition of claim 5.

19. A method of dyeing hair comprising the step of applying to the hair an oxidative composition of claim 6.

20. An oxidative hair dye composition of claim 1, 3 or 6 wherein the primary intermediate is selected from the group consisting of ortho- and para-phenylenediamines; heterocyclic bases, and ortho- and para-aminophenols selected from the group consisting of o-aminophenol, 5-chloro-o-aminophenol, p-aminophenol, 2-methyl-p-aminophenol, 2,3-dimethyl-p-aminophenol, 2,6-dimethyl-p-aminophenol, 3-methoxy-p-aminophenol, 2-chloro-p-aminophenol, N-methyl-p-aminophenol and 2-(methylthio)-p-aminophenol.

21. A package of claim 7, 9 or 12 wherein the primary intermediate is selected from the group consisting of ortho- and para-phenylendiamines; heterocyclic bases, and ortho- and para-aminophenols selected from the group consisting of o-aminophenol, 5-chloro-o-aminophenol, p-aminophenol, 2-methyl-p-aminophenol, 2,3-dimethyl-p-aminophenol, 2,6-dimethyl-p-aminophenol, 3-methoxy-p-aminophenol, 2-chloro-p-aminophenol, N-methyl-p-aminophenol and 3-(methylthio)-p-aminophenol.

22. A method of dyeing hair comprising the step of applying to the hair an oxidative composition of claim 20.

* * * * *